United States Patent [19]

Angulo

[11] Patent Number: 5,133,721
[45] Date of Patent: Jul. 28, 1992

[54] DEVICE FOR REMOVING FOREIGN OBJECTS FROM ANATOMIC ORGANS

[75] Inventor: Earl D. Angulo, Silver Spring, Md.

[73] Assignee: The United States of America as represented by the Administrator of the National Aeronautics and Space Administration, Washington, D.C.

[21] Appl. No.: 674,828

[22] Filed: Mar. 19, 1991

[51] Int. Cl.⁵ .............................................. A61M 1/00
[52] U.S. Cl. ................................ 606/106; 148/402; 606/78; 606/127
[58] Field of Search .................. 606/106, 78, 27–31, 606/113, 127, 128; 148/402; 604/95

[56] References Cited

U.S. PATENT DOCUMENTS

| 3,285,470 | 11/1966 | Frei et al. ................ 148/402 X |
| 3,489,151 | 1/1970 | Eller . |
| 3,581,745 | 6/1971 | Eller . |
| 3,802,930 | 4/1974 | Brook et al. ............. 148/402 X |
| 3,868,956 | 3/1975 | Alfidi ...................... 606/78 X |
| 3,980,861 | 9/1976 | Fukunaga . |
| 4,485,816 | 12/1984 | Krumme .................. 606/78 X |
| 4,753,689 | 6/1988 | Rizzo et al. ............. 148/402 X |
| 4,925,445 | 5/1990 | Sakamoto et al. ............ 604/95 |
| 5,025,799 | 6/1991 | Wilson ................... 604/95 X |

OTHER PUBLICATIONS

Encyclopedia of Materials Science & Engineering, vol. 6, 1986, pp. 4365–4374, Pergamon Press.

Primary Examiner—Peter A. Aschenbrenner
Attorney, Agent, or Firm—Paul S. Clohan, Jr.; R. Dennis Marchant; Guy M. Miller

[57] ABSTRACT

A device for removing foreign objects from anatomic organs such as the ear canal or throat having a housing shaped like a flashlight, an electrical power source such as a battery or AC power from a wall socket, and a tip extending from the housing, the tip having at least one wire loop made from a shape-memory-effect alloy such as Nitinol switchably connected to the electrical power source such that when electric current flows through the wire loop the wire loop heats up and returns to a previously programmed shape such as a curet or tweezers so as to facilitate removal of the foreign object.

9 Claims, 6 Drawing Sheets

DEVICE FOR REMOVING FOREIGN OBJECTS FROM ANATOMIC ORGANS

ORIGIN OF THE INVENTION

The invention described herein was made by an employee of the United States Government, and may be manufactured and used by or for the Government for governmental purposes without the payment of any royalties thereon or therefor.

TECHNICAL FIELD

This invention relates to instruments for removing obstacles from anatomic organs and more particularly to a device for removing foreign objects from the ear canal, nose or throat.

BACKGROUND ART

Previous methods for removing foreign objects from anatomic organs involved the use of forceps, curet, pressurized water, suction devices and/or magnets. For example, one device for removing obstructions from the throat comprises two generally coextensive arms hinged together at one end of each, enabling a forceps or tweezer-like movement of the other or free ends. The arms have insertable portions terminating in the free ends and being similarly curved in the general planes of the arms for insertion into a throat associated organ on opposite sides of an obstruction therein. The insertable portions have spur-like obstruction-engageable means extending from each insertable portion inner face. The end regions of the insertable portions are curled inwardly toward each other.

Another instrument for removing obstructions from the throat comprised a generally U-shaped instrument for removing obstructing objects from the throat and organs associated therewith and has spaced arms which can be squeezed together. The arms are formed with curved hooklike ends having lateral flanges to protect the tongue and parts of the throat when the instrument is inserted in the throat. Wedge-shaped spurs extend laterally from inner sides of the arms to interfit with each other for engaging the obstruction. The spurs can be pivotally mounted.

The disadvantages of the prior art involve the need, in most cases, to insert a relatively large instrument past the foreign object in order to grasp it. This can be a dangerous and frustrating task for the physician. Unsuccessful traumatic attempts to force the instrument past the object can also lead to significant damage to the anatomic canal; e.g., in the ear canal possible perforation of the tympanic membrane and loss of hearing can result.

STATEMENT OF THE INVENTION

It is therefore an object of the present invention to provide a device for removing foreign objects from anatomic organs that allows the physician to safely capture the foreign object and remove it from the anatomic canal without the use of a large clumsy instrument.

The foregoing object is achieved by providing a device that eliminates the necessity of forcing a relatively large and rigid instrument, such as tweezers, forceps, or a curet, past the foreign object so the object can be pulled from the ear, nose or throat canal. The present invention uses a flat loop of very small (approximately 0.010" diameter or less) and flexible shape-memory-effect wire (such as Nitinol) which is relatively safe and easy to slip past the foreign object. When the flat tip of the wire loop is inserted beyond the foreign object electrical current is allowed to pass through the wire which causes it to heat up to slightly above body temperature and, due to the shape-memory-effect, to form a hook or curet if a single wire loop is used, or tweezers if two loops are used. This allows the physician to capture or grasp the foreign object and easily remove it. Thus the danger of damaging the ear, nose or throat canal is greatly reduced when compared to prior art devices.

BRIEF DESCRIPTION OF THE DRAWINGS

FIG. 5a is an enlarged elevation view of the cool barbed tip filament wire loop shown in FIG. 4a.

FIG. 7a is an enlarged elevation view of the cool forcep tip filament wire loop shown in FIG. 6a.

FIG. 8b is an enlarged view of the tip of FIG. 8a.

FIG. 9b is an enlarged view of the tip of FIG. 9a.

DETAILED DESCRIPTION OF THE INVENTION

Figure 1:
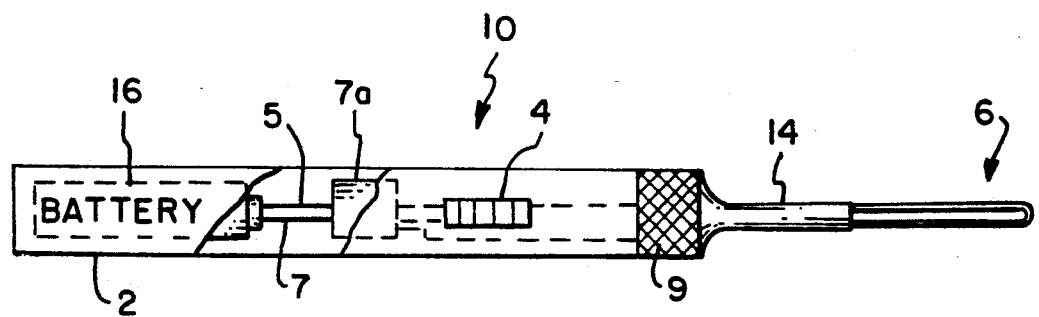
FIG. 1 is a plan view of a device to remove foreign objects from an anatomic organ according to the present invention.

Referring now to FIG. 1, a device 10 for removing foreign objects from anatomic organs according to the teachings of the present invention is shown. Device 10 includes a generally cylindrical housing 2, which is similar to a flashlight housing only smaller in diameter, a tip 14, and a thermal tip 6. Tip 14 can be made removeable as represented by knurled area 9 which would allow the user to unscrew tip 14. Within housing 2 is a battery 16 controlled by on-off switch 4. Battery 16 is connected to thermal tip 6 by wires 5 and 7 and is a DC power source for device 10, although other power sources can be used as described later. Instead of providing electrical current to the filament of a light bulb (as in a flashlight), in device 10 battery 16 provides DC current through a standard current limiting circuit 7a to thermal tip 6. Thermal tip 6 is made from a shape-memory-effect alloy such as Nitinol. When an ordinary metal is strained beyond its elastic limit, permanent deformation of the material is produced. For most metals, this yield point corresponds to a fraction of a percent strain; any strain beyond this is defined as plastic deformation and is expected to remain. For example, if an extensively kinked metal wire were heated it would not straighten out spontaneously. Yet this is exactly what certain metallic alloys are able to do. If one of these alloys is deformed (below a critical temperature, with a limit of about 10% strain), it will recover its original unbent shape when it is reheated. The reheating "reminds" the alloy that it prefers a different crystal structure and associated shape at higher temperature. This unusual behavior has been termed the shape-memory-effect. Shape-memory-effect alloy is a common feature of most alloys which are susceptible to a martensitic transformation. Typical shape-memory-effect alloy compositions are given below in Table 1. Although the shape-memory-effect has recently been widely publicized for Nitinol (Ti-Ni) alloys, historically the shape-memory-effect was first extensively studied in an alloy of gold and cadmium. It is the shape-memory-effect in Nitinol, however, that has stimulated widespread interest in its potential application. For example, Nitinol has been used in orthopedic devices, vena cava filters, artificial hearts and for an intracranial aneurism clip. The shape-memory-effect programming sequence of the alloys is well understood in the art and requires no further discussion here.

TABLE 1

Typical shape-memory-effect alloy compositions (wt%)

Figure 2:
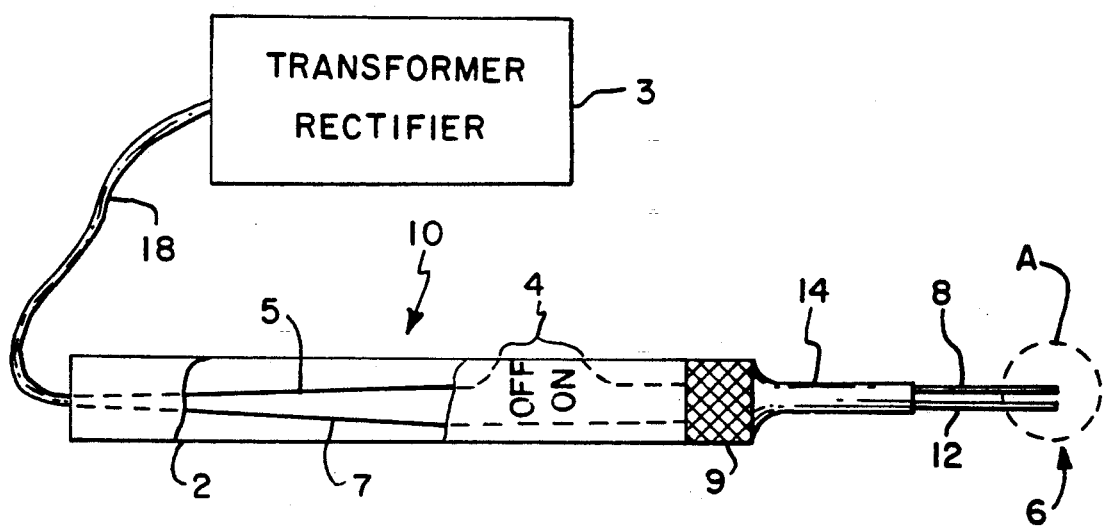
FIG. 2 is an elevation view of the device shown in FIG. 1.

Au-(34–36%)Cd
(40–62.8%)Au-(10.5–27%)Cu-(26.6–33%)Zn
Cu-(38–40%)Zn
Cu-(20–32%)Zn/Al
Cu-17%Zn-7%Al
Cu-44%Al
Cu-34.5%Zn-0.9%Si
Cu-(14–15%)Al-3%Ni
Cu-25%Sn
Ti-(55–58%)Ni
(45–46%)Ti-($\leq$22%)Cu-Ni(balance)
45%Ti-($\leq$8%)Co-Ni(balance)
Ni-26.5%Al Referring now to FIG. 2, an elevation view of device 10 is now shown. As an alternate to battery 16 power, standard AC power could be used, as shown by AC power cord 18 and transformer/rectifier 3. It can now be seen in this view that thermal tip 6 consists of two filament wire loops 8 and 12 that, when heated, will form tweezers, i.e., the filament wire loops have been programmed according to standard shape-memory-effect techniques to return to the shape of tweezers when heated to slightly above body temperature. The Nitinol or other shape-memory-effect wire used in filament wire loops 8 and 12 is preferably made from very small diameter Nitinol wire approximately 0.010" in diameter and is approximately 1" long by 0.40" wide which allows thermal tip 6 to easily slip beyond the foreign object to be removed. Depending upon the particular application of device 10, the wire diameter and the length and width of thermal tip 6 can easily be varied.

Figure 3:
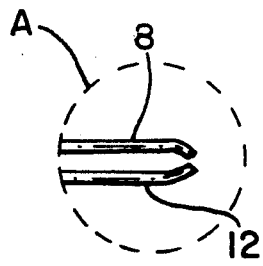
FIG. 3 is an enlarged view of the tip of the device of FIGS. 1 and 2.
Figure 4A:
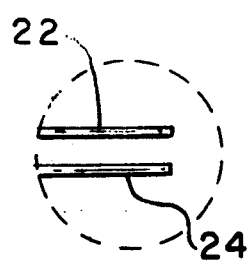
FIG. 4a is an enlarged plan view of a cool barbed tip filament wire loop.
Figure 4B:
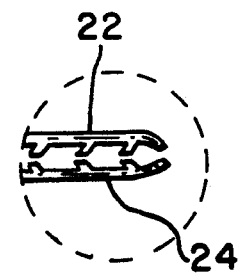
FIG. 4b is an enlarged plan view of a warm barbed tip filament wire loop.
Figure 5A:
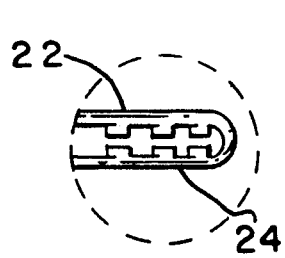
Figure 5B:
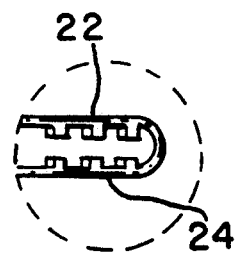
FIG. 5b is an enlarged elevation view of the warm barbed tip filament wire loop shown in FIG. 4b.
Figure 6A:
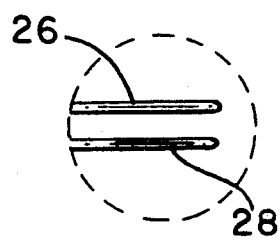
FIG. 6a is an enlarged plan view of a cool forcep tip filament wire loop.
Figure 6B:
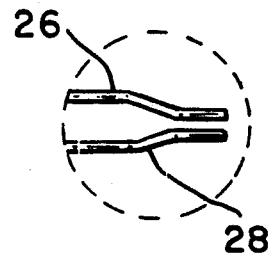
FIG. 6b is an enlarged plan view of a warm forcep tip filament wire loop.
Figure 7A:
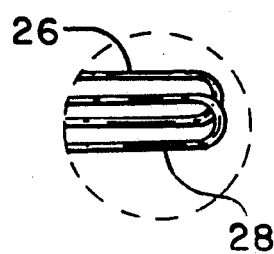
Figure 7B:
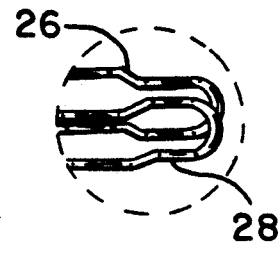
FIG. 7b is an enlarged elevation view of the warm forcep tip filament wire loop shown in FIG. 6b.
Figure 8A:
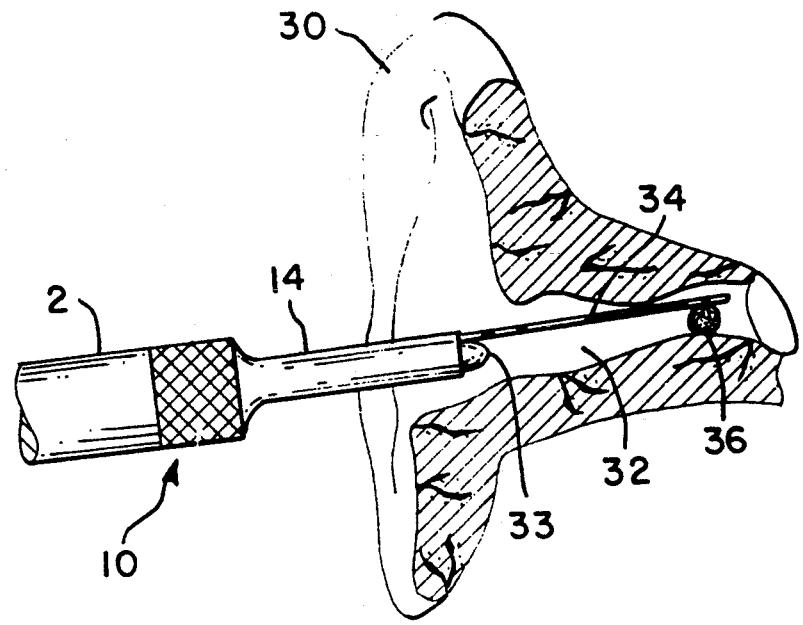
FIG. 8a is a view of a device with a curet thermal tip in an ear canal when the thermal tip is cool.
Figure 8B:
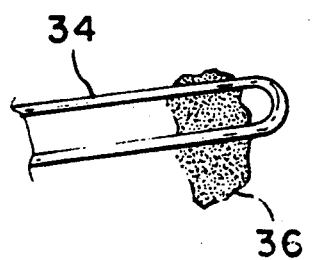
Figure 8C:
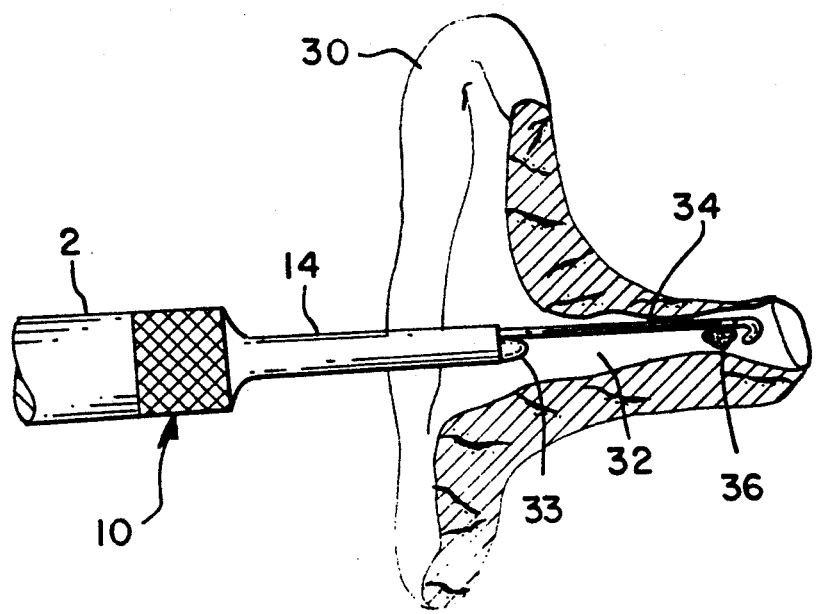
FIG. 8c is a view of the device of FIG. 8a in an ear canal when the thermal tip is warm.
Figure 8D:
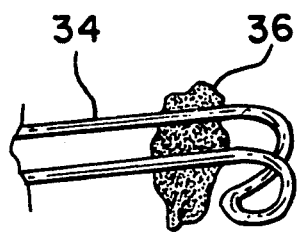
FIG. 8d is an enlarged view of the tip of FIG. 8c.
Figure 9A:
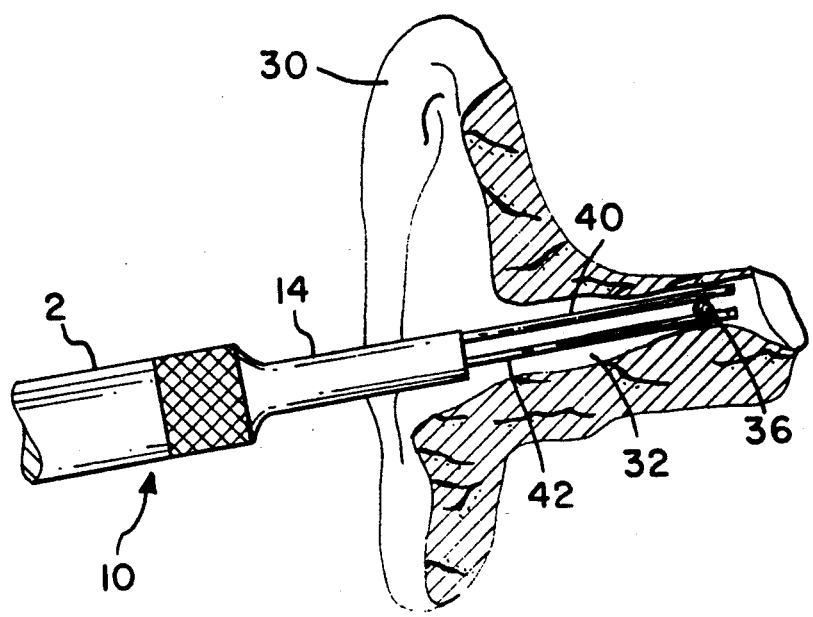
FIG. 9a is a view of a device with a tweezers thermal tip in an ear canal when the thermal tip is cool.
Figure 9B:
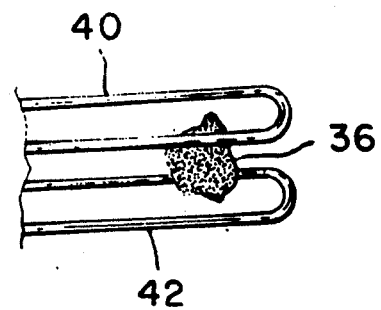
Figure 9C:
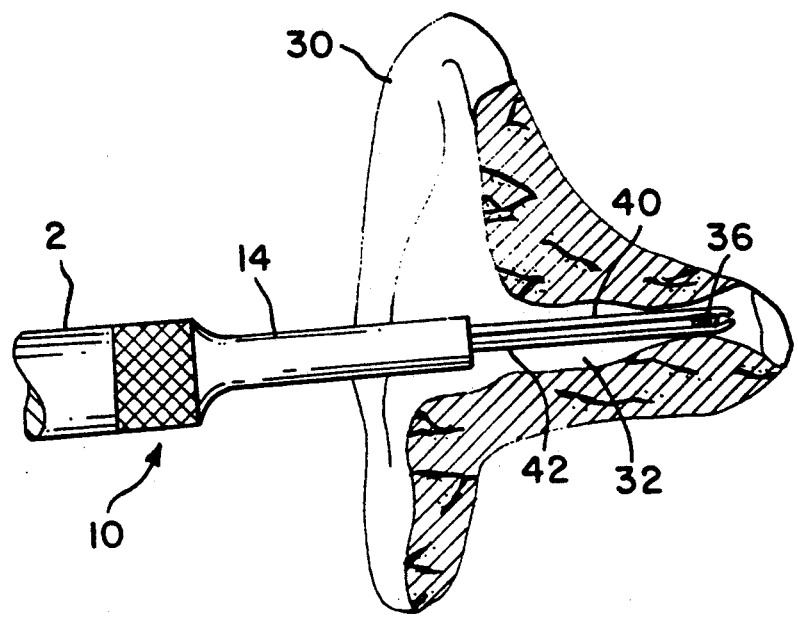
FIG. 9c is another view of the device of FIG. 9a in an ear canal when the thermal tip is warm.
Figure 9D:
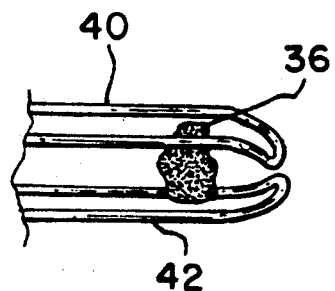
FIG. 9d is an enlarged view of the tip of FIG. 9c.

An enlarged view of thermal tip 6 (area A on FIG. 2) is shown in FIG. 3, which depicts filament wire loops 8 and 12 in a warm condition caused by the DC current through filament wire loops 8 and 12. Because of the previous programming of the Nitinol wire used in filament wire loops 8 and 12, their tips have now come together, as tweezers do, to grasp the foreign object. When the electric current is removed, the tips of the filament wire loops 8 and 12 will return to their previous straight configuration. Alternate embodiments for thermal tip 6 are shown in FIGS. 4a through 7b. FIG. 4a through 5b shows a pair of barbed tip filament loops 22 and 24 made from flat wire or stamped from 0.010" thick sheet. FIG. 4a is an enlarged plan view of barbed tip filament wire loops 22 and 24 when they are cool. FIG. 4b is an enlarged plan view of barbed tip filament wire loops 22 and 24 when they are warm. FIG. 5a is an enlarged elevation view of barbed tip filament wire loops 22 and 24 when they are cool. And FIG. 5b is an enlarged elevation view of barbed tip filament wire loops 22 and 24 when they are warm. FIG. 6a through 7b shows a pair of forcep tip filament wire loops 26 and 28. FIG. 6a is an enlarged plan view of forcep tip filament wire loops 26 and 28 when they are cool. FIG. 6b is an enlarged plan view of forcep tip filament wire loops 26 and 28 when they are warm. FIG. 7a is an enlarged elevation view of forcep tip filament wire loops 26 and 28 when they are cool. And FIG. 7b is an enlarged elevation view of forcep tip filament wire loops 26 and 28 when they are warm. Referring now to FIG. 8a, an additional alternate embodiment of device 10 is shown in use. Instead of two filament wire loops this embodiment has only one filament wire loop 34 which is shown as it is placed beyond foreign object 36. A close-up is shown in FIG. 8b. This embodiment also has a light bulb 33 in tip 14 to provide additional illumination of foreign object 36 lodged in ear canal 32 of ear 30. When electric current from the power source is supplied to the single filament wire loop 34, it becomes warm, the tip curls and forms a curet, as shown in FIGS. 8c and 8d. Foreign object 36 can then be captured and withdrawn from ear canal 32. FIGS. 9a through 9d show removal of foreign object 36 from ear canal 32 when two filament wire loops 40 and 42 are provided. In this embodiment, the two filament wire loops 40 and 42 form tweezers when heated, enabling the operator to grasp and remove foreign object 36 easily.

To those skilled in the art, many modifications and variations of the present invention are possible in light of the above teachings. It is therefore to be understood that the present invention can be practiced otherwise than as specifically described herein and still will be within the spirit and scope of the appended claims.

I claim:

1. A device for removing foreign objects from anatomic organs comprising:
   a housing;
   an electrical power source;
   a tip extending from said housing, said tip comprising at least one wire loop made from a shape-memory-effect alloy switchably connected to said electrical power source such that when electric current flows through said wire loop said wire loop heats up and returns to a previously programmed shape so as to facilitate removal of said foreign object; and further comprising a light bulb located on said housing so as to illuminate said tip.

2. The device of claim 1 wherein said electrical power source comprises a battery and current limiting circuit located within said housing.

3. The device of claim 1, wherein said electrical power source comprises an AC power cord with a transformer/rectifier for connection to a wall socket.

4. The device of claim 1 wherein said previously programmed shape comprises a curet shape.

5. The device of claim 1, wherein said tip comprises two wire loops made from shape-memory-effect alloys switchably connected to said electrical power source.

6. The device of claim 5 wherein said two wire loops return to a previously programmed shape of tweezers.

7. The device of claim 5 wherein said two wire loops return to a previously programmed shape of forceps.

8. The device of claim 6 further comprising barbs on said wire loops.

9. The device of claim 1 wherein said shape-memory-effect alloy is Nitinol.

* * * * *